(12) United States Patent
Chen et al.

(10) Patent No.: US 12,117,452 B2
(45) Date of Patent: Oct. 15, 2024

(54) IDENTIFICATION OF HOST CELL PROTEINS

(71) Applicant: Regeneron Pharmaceuticals, Inc., Tarrytown, NY (US)

(72) Inventors: I-Hsuan Chen, Redwood City, CA (US); Hui Xiao, Scarsdale, NY (US); Ning Li, New Canaan, CT (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 956 days.

(21) Appl. No.: 16/850,363

(22) Filed: Apr. 16, 2020

(65) Prior Publication Data

US 2020/0333353 A1 Oct. 22, 2020

Related U.S. Application Data

(60) Provisional application No. 62/835,065, filed on Apr. 17, 2019.

(51) Int. Cl.
*G01N 33/68* (2006.01)
*G01N 1/40* (2006.01)

(52) U.S. Cl.
CPC ....... *G01N 33/6848* (2013.01); *G01N 1/4005* (2013.01); *G01N 2458/15* (2013.01); *G01N 2560/00* (2013.01)

(58) Field of Classification Search
CPC ............. G01N 33/6848; G01N 1/4005; G01N 2458/15; G01N 2560/00
See application file for complete search history.

(56) References Cited

U.S. PATENT DOCUMENTS

| | | | |
|---|---|---|---|
| 2010/0261215 A1* | 10/2010 | Mehul | G01N 33/6848 435/23 |
| 2011/0244445 A1* | 10/2011 | Moritz | B01D 15/3823 435/7.1 |
| 2016/0176921 A1* | 6/2016 | Rajendran | C07K 16/18 530/387.3 |
| 2019/0169675 A1* | 6/2019 | Graham | C12Q 1/37 |

FOREIGN PATENT DOCUMENTS

| | | |
|---|---|---|
| WO | WO 2009/044903 A1 | 4/2009 |
| WO | WO 2018/031858 A1 | 2/2018 |

OTHER PUBLICATIONS

Hall, Troii, et al. "Polysorbates 20 and 80 Degradation by Group XV Lysosomal Phospholipase a 2 Isomer X1 in Monoclonal Antibody Formulations." Journal of Pharmaceutical Sciences, vol. 105, No. 5, Apr. 5, 2016, pp. 1633-1642., https://doi.org/10.1016/j.xphs.2016.02.022. (Year: 2016).*

Reisinger, Veronika, et al. "A Mass Spectrometry-Based Approach to Host Cell Protein Identification and Its Application in a Comparability Exercise." Analytical Biochemistry, vol. 463, Mar. 6, 2014, pp. 1-6., https://doi.org/10.1016/j.ab.2014.06.005. (Year: 2014).*

(Continued)

*Primary Examiner* — Jennifer Wecker
*Assistant Examiner* — Ali Husain Faraz
(74) *Attorney, Agent, or Firm* — Kramer Levin Naftalis & Frankel LLP

(57) ABSTRACT

Method of identifying host-cell proteins in a sample matrix are provided.

19 Claims, 8 Drawing Sheets

(56) References Cited

OTHER PUBLICATIONS

Vivek Joshi et al. "Filtration as a Sample Preparation Technique Prior to Mass Spectrometry: Selecting the Right 4 Filtration Device" In: "Sample Preparation in Biological Mass Spectrometry", Jan. 1, 2011 (Jan. 1, 2011), Springer Netherlands, Dordrecht, pp. 61-75 (Year: 2011).*

Hall, Troii, et al. "Polysorbates 20 and 80 Degradation by Group XV Lysosomal Phospholipase a 2 IsomerXI in Monoclonal Antibody Formulations." Journal of Pharmaceutical Sciences, vol. 105, No. 5, Apr. 5, 2016, pp. 1633-1642., https://doi.org/10.1016/j.xphs 2016.02.022 (Year: 2016).*

Farrell, Amy, et al. "Quantitative host cell protein analysis using two dimensional data independent LC-MS." Analytical Chemistry, vol. 87, No. 18, Aug. 17, 2015, pp. 9186-9193, https://doi.org/10.1021/acs.analchem.5b01377 (Year: 2015).*

Reisinger Veronika et al: "A mass spectrometry-based approach to host cell protein identification and its application in a comparability exercise," Analytical Biochemistry, Academic Press, Amsterdam, NL, vol. 463, Jun. 17, 2014 (Jun. 17, 2014), pp. 1-6.

TR011 Hall et al: "Polysorbates 20 and 80 Degradation by Group XV Lysosomal Phospholipase A 2 Isomer X1 in Monoclonal Antibody Formulations," Journal of Pharmaceutical Sciences, vol. 105, No. 5, May 1, 2016 (May 1, 2016), pp. 1633-1642.

I-Hsuan Chen et al: "Improved Host Cell Protein Analysis in Monoclonal Antibody Products through Molecular Weight Cutoff Enrichment," Analytical Chemistry, vol. 92, No. 5, Jan. 30, 2020 (Jan. 30, 2020), pp. 3751-3757.

Vivek Joshi et al: "Filtration as a Sample Preparation Technique Prior to Mass Spectrometry: Selecting the Right Filtration Device" In: "Sample Preparation in Biological Mass Spectrometry", Jan. 1, 2011 (Jan. 1, 2011), Springer Netherlands, Dordrecht, pp. 61-75.

International Search Report Application No. PCT/US2020/028458, International Filing Date Apr. 16, 2020, Date of Mailing Jul. 8, 2020.

* cited by examiner

IDENTIFICATION OF HOST CELL PROTEINS

FIELD

The invention generally pertains to methods for identifying host cell proteins.

BACKGROUND

Protein-based biopharmaceutical products have emerged as important drugs for the treatment of cancer, autoimmune disease, infection and cardiometabolic disorders, and they represent one of the fastest growing product segments of the pharmaceutical industry. Protein-based biopharmaceutical products must meet very high standards of purity. Thus, it can be important to monitor any impurities in such biopharmaceutical products at different stages of drug development, production, storage and handling.

For example, host cell proteins (HCPs) can be present in protein-based biopharmaceuticals which are developed using cell-based systems. The presence of HCPs in drug products need to be monitored and can be unacceptable above a certain amount. Analytical methods for assays for characterization of HCPs should display sufficient accuracy and resolution. Direct analysis can require isolation of the product in a sufficiently large amount for the assay, which is undesirable and has only been possible in selected cases. Hence, it is a challenging task to determine the workflow and analytical tests to characterize HCPs in a sample when mixed with overwhelmingly high concentration of active drug. From the foregoing it will be appreciated that a need exists for improved methods for characterizing HCPs in a sample.

SUMMARY

A key criterion in developing biopharmaceutical products can be to monitor impurities in the product. When such impurities do occur, their identification and quantification constitutes an important step in the bioprocess.

Exemplary embodiments disclosed herein satisfy the aforementioned demands by providing methods for identifying host-cell protein(s).

In one exemplary embodiment, the method of identifying a host-cell protein in a sample matrix having a protein of interest can comprise dissociating a host cell protein from a protein of interest and filtering the dissociated host-cell protein using a molecular weight cut-off filter. In one aspect of this embodiment, the protein dissociation can be carried out using a protein dissociating agent. In a specific aspect of this embodiment, the protein dissociating agent can comprise sodium deoxycholate. In another specific aspect of this embodiment, the protein dissociating agent can comprise N-lauroylsarcosine. In yet another specific aspect of this embodiment, the protein dissociating agent can comprise sodium deoxycholate and N-lauroylsarcosine. In a specific aspect of this embodiment, the protein dissociating agent can be degradable in nature. In one aspect of this embodiment, the molecular weight cut-off filter can have a cutoff of at least about 100 KDa. In another aspect of this embodiment, the molecular weight cut-off filter can have a cutoff of at least about 50 KDa. In one aspect of this embodiment, the method can be configured to detect host-cell proteins which are at a concentration of at least about 1 ppm. In one aspect of this embodiment, the filtering step enriches the dissociated host-cell protein by at least about 50-fold. In one aspect of this embodiment, the method of identifying a host-cell protein in a sample matrix can optionally comprise contacting the filtered host-cell protein to a hydrolyzing agent. In another aspect of this embodiment, the method of identifying a host-cell protein in a sample matrix can optionally comprise identifying the host-cell protein using a mass spectrometer.

In one exemplary embodiment, the method of identifying a host-cell protein in a sample matrix having a protein of interest can comprise dissociating a host cell protein from a protein of interest, filtering the dissociated host-cell protein using a molecular weight cut-off filter, and contacting the filtered host-cell protein to a hydrolyzing agent. In one aspect of this embodiment, the protein dissociation can be carried out using a protein dissociating agent. In a specific aspect of this embodiment, the protein dissociating agent can comprise sodium deoxycholate. In another specific aspect of this embodiment, the protein dissociating agent can comprise N-lauroylsarcosine. In yet another specific aspect of this embodiment, the protein dissociating agent can comprise sodium deoxycholate and N-lauroylsarcosine. In a specific aspect of this embodiment, the protein dissociating agent can be degradable in nature. In one aspect of this embodiment, the molecular weight cut-off filter can have a cutoff of at least about 100 KDa. In one aspect of this embodiment, the molecular weight cut-off filter can have a cutoff of at least about 50 KDa. In one aspect of this embodiment, the method can be configured to only detect host-cell proteins which are at a concentration of a detection limit of the method can be at least about 1 ppm. In one aspect of this embodiment, the filtering step enriches the dissociated host-cell protein by at least about 50-fold. In one aspect of this embodiment, the method of identifying a host-cell protein in a sample matrix can optionally comprise contacting the filtered host-cell protein to a hydrolyzing agent. In another aspect of this embodiment, the method of identifying a host-cell protein in a sample matrix can optionally comprise identifying the host-cell protein using a mass spectrometer. In one aspect of this embodiment, the hydrolyzing agent can be trypsin. In one aspect of this embodiment, the method can further comprise contacting the filtered host-cell protein to a protein reducing agent. In a specific aspect of this embodiment, the protein reducing agent can be TCEP. In another aspect of this embodiment, the method can further comprise contacting the filtered host-cell protein to a protein alkylating agent. In a specific aspect of this embodiment, the protein alkylating agent can be CAA. In yet another aspect of this embodiment, the method can further comprise centrifuging the filtered host-cell protein.

In one exemplary embodiment, the method of identifying a host-cell protein in a sample matrix having a protein of interest can comprise dissociating a host cell protein from a protein of interest, filtering the dissociated host-cell protein using a molecular weight cut-off filter and identifying the host-cell protein. In one aspect of this embodiment, the protein dissociation of can be carried out using a protein dissociating agent. In one aspect of this embodiment, the protein dissociation can be carried out using a protein dissociating agent. In a specific aspect of this embodiment, the protein dissociating agent can comprise sodium deoxycholate. In another specific aspect of this embodiment, the protein dissociating agent can comprise N-lauroylsarcosine. In yet another specific aspect of this embodiment, the protein dissociating agent can comprise sodium deoxycholate and N-lauroylsarcosine. In a specific aspect of this embodiment, the protein dissociating agent can be degradable in nature. In one aspect of this embodiment, the molecular weight cut-off filter can have a cutoff of at least about 100 KDa. In one aspect of this embodiment, the molecular weight cut-off filter can have a cutoff of at least about 50 KDa. In one aspect of this embodiment, the identification of the host-cell protein can be carried out using a mass spectrometer. In a specific aspect of this embodiment, the mass spectrometer can be coupled to a liquid chromatography system. In another specific aspect of this embodiment, the liquid chromatography system can be a nano liquid chromatography system. In another specific aspect of this embodiment, the mass spectrometer can be a tandem mass spectrometer. In one aspect of this embodiment, the method can be configured to detect host-cell proteins which are at a concentration of at least about 1 ppm. In one aspect of this embodiment, the filtering step enriches the dissociated host-cell protein by at least about 50-fold. In one aspect of this embodiment, the method of identifying a host-cell protein in a sample matrix can optionally comprise contacting the filtered host-cell protein to a hydrolyzing agent.

In one exemplary embodiment, the method of identifying a host-cell protein in a sample matrix having a protein of interest can comprise dissociating a host cell protein from a protein of interest, filtering the dissociated host-cell protein using a molecular weight cut-off filter, contacting the filtered host-cell protein to a hydrolyzing agent and identifying the host-cell protein. In one aspect of this embodiment, the protein dissociation can be carried out using a protein dissociating agent. In a specific aspect of this embodiment, the protein dissociating agent can comprise sodium deoxycholate. In another specific aspect of this embodiment, the protein dissociating agent can comprise N-lauroylsarcosine. In yet another specific aspect of this embodiment, the protein dissociating agent can comprise sodium deoxycholate and N-lauroylsarcosine. In a specific aspect of this embodiment, the protein dissociating agent can be degradable in nature. In one aspect of this embodiment, the molecular weight cut-off filter can have a cutoff of at least about 100 KDa. In one aspect of this embodiment, the molecular weight cut-off filter can have a cutoff of at least about 50 KDa. In one aspect of this embodiment, the hydrolyzing agent can be trypsin. In one aspect of this embodiment, the method can be configured to detect host-cell proteins which are at a concentration of at least about 1 ppm. In one aspect of this embodiment, the filtering step enriches the dissociated host-cell protein by at least about 50-fold. In one aspect of this embodiment, the identification of the host-cell protein can be carried out using a mass spectrometer. In a specific aspect of this embodiment, the mass spectrometer can be coupled to a liquid chromatography system. In another specific aspect of this embodiment, the liquid chromatography system can be a nano liquid chromatography system. In another specific aspect of this embodiment, the mass spectrometer can be a tandem mass spectrometer. In one aspect of this embodiment, the method can further comprise contacting the filtered host-cell protein to a protein reducing agent. In a specific aspect of this embodiment, the protein reducing agent can be TCEP. In another aspect of this embodiment, the method can further comprise contacting the filtered host-cell protein to a protein alkylating agent. In a specific aspect of this embodiment, the protein alkylating agent can be CAA. In yet another aspect of this embodiment, the method can further comprise centrifuging the filtered host-cell protein.

DETAILED DESCRIPTION

Figure 1:
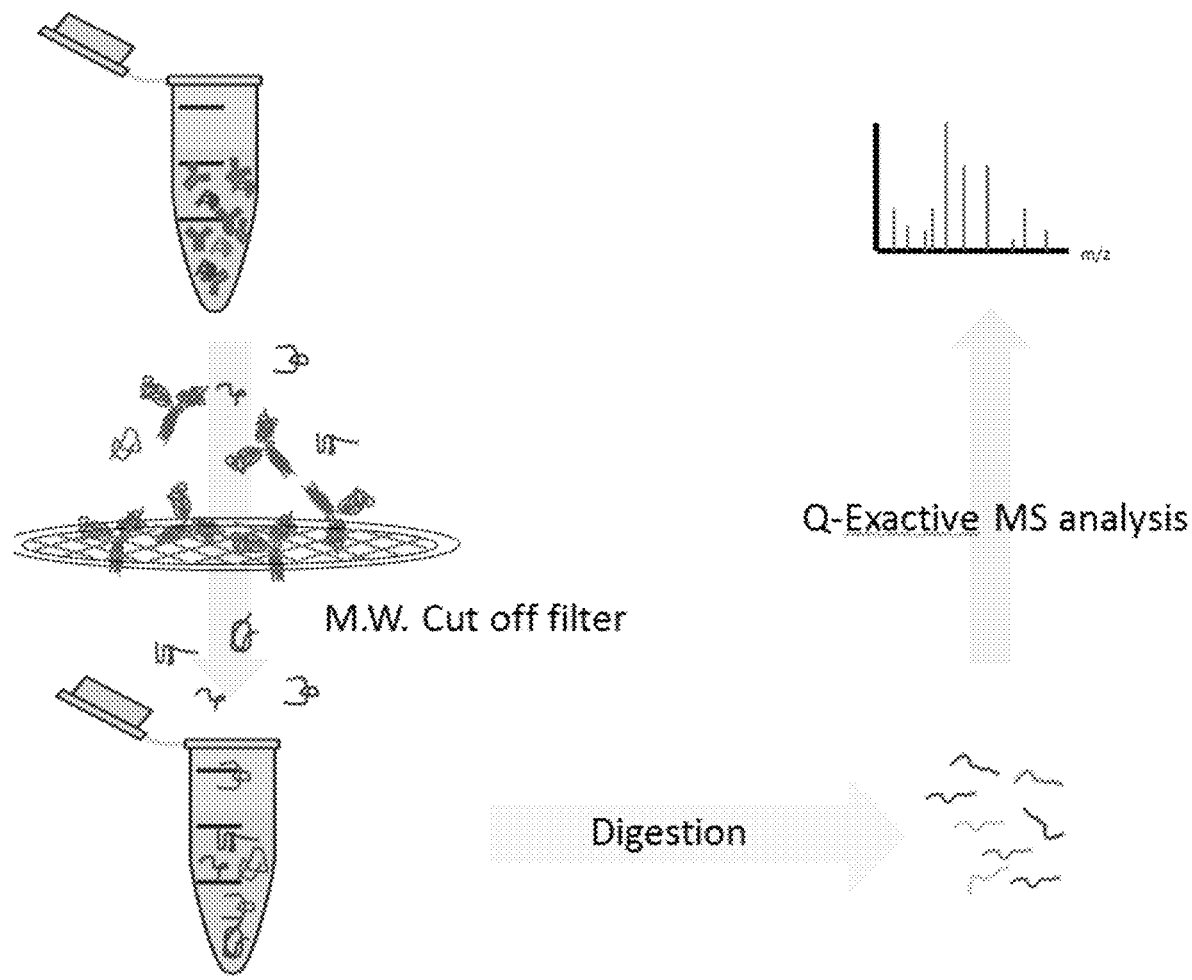
FIG. 1 shows the experimental workflow of HCP (host-cell protein) identification using molecular weight cut-off filtration according to an exemplary embodiment.

Since the first therapeutic monoclonal antibody (mAb), muromona-CD3 was approved by FDA in 1992 to treat organ transplant patients with acute rejection, more than 80 therapeutic mAbs have been approved for clinical use with great success. During cell-based production of these therapeutic proteins, the final protein based drug product must be highly purified so that impurities from cell are at acceptable low levels before clinical use. The impurities, in particular, host cell proteins (HCPs) derived from mammalian expression system (e.g., Chinese hamster ovary (CHO) cells) are required to be monitored. The general guidelines for HCPs level in the final drug substance are less than 100 ppm (John H. Chon & Gregory Zarbis-Papastoitsis, *Advances in the production and downstream processing of antibodies*, 28 NEW BIOTECHNOLOGY 458-463 (2011)). However, even total HCPs impurities present at low levels in drug substance, the trace amount of HCPs may not be acceptable for some particular HCPs that may cause the immune response, being toxic or biologically active after injection (J. R. Bierich, *Treatment of Pituitary Dwarfism with Biosynthetic Growth Hormone*, 75 ACTA PAEDIATRICA 13-18 (1986); T. Romer et al., *Efficacy and safety of a new ready-to-use recombinant human growth hormone solution*, 30 JOURNAL OF ENDOCRINOLOGICAL INVESTIGATION 578-589 (2007); Daniel G. Bracewell, Richard Francis & C. Mark Smales, *The future of host cell protein (HCP) identification during process development and manufacturing linked to a risk-based management for their control*, 112 BIOTECHNOLOGY AND BIOENGINEERING 1727-1737 (2015); Saloumeh Kadkhodayan Fischer et al., *Specific Immune Response to Phospholipase B-Like 2 Protein, a Host Cell Impurity in Lebrikizumab Clinical Material*, 19 THE AAPS JOURNAL 254-263 (2016)). It may also be intolerable if HCPs pertain the potency to degrade antibody or alter the antibody binding potency (Nitin Dixit et al., *Residual Host Cell Protein Promotes Polysorbate 20 Degradation in a Sulfatase Drug Product Leading to Free Fatty Acid Particles*, 105 JOURNAL OF PHARMACEUTICAL SCIENCES 1657-1666 (2016); Troii Hall et al., *Polysorbates 20 and 80 Degradation by Group XV Lysosomal Phospholipase A2 Isomer X1 in Monoclonal Antibody Formulations.*, 105 JOURNAL OF PHARMACEUTICAL SCIENCES 1633-1642)). Therefore, it can be desirable to have methods that are able to monitor all HCP components individually.

Traditionally, the enzyme-linked immunosorbent assay (ELISA) with polyclonal anti-HCP antibodies has been used to quantify the overall HCPs abundance (Denise C. Krawitz et al., *Proteomic studies support the use of multi product immunoassays to monitor host cell protein impurities*, 6 PROTEOMICS 94-110 (2006); Catherine Em Hogwood, Daniel G Bracewell & C Mark Smales, *Host cell protein dynamics in recombinant CHO cells*, 4 BIOENGINEERED 288-291 (2013)). Given the demand for measures of individual HCP components, ELISA might not be the final solution for evaluating level of HCPs. In addition, some weakly or nonimmunogenic HCPs may not generate antibodies for ELISA detection, these HCPs are therefore not able to be detected.

A number of complementary analytical approaches have been employed to monitor HCPs, including 1D/2D-PAGE and mass spectrometry based analytical technology (Julita K. Grzeskowiak et al., *Two-dimensional fluorescence difference gel electrophoresis for comparison of affinity and non-affinity based downstream processing of recombinant monoclonal antibody*, 1216 JOURNAL OF CHROMATOGRAPHY A 4902-4912 (2009); Catalin Doneanu et al., *Analysis of host-cell proteins in biotherapeutic proteins by comprehensive online two-dimensional liquid chromatography/mass spectrometry*, 4 MABS 24-44 (2012); Mi Jin et al., *Profiling of host cell proteins by two-dimensional difference gel electrophoresis (2D-DIGE): Implications for downstream process development*, 105 BIOTECHNOLOGY AND BIOENGINEERING 306-316 (2010)). Liquid chromatography coupled tandem mass spectrometry (LC-MS/MS) can also provide a means for both identification and quantification on HCP impurities simultaneously and has emerged as the major orthogonal method to complement the ELISA assay. However, a major challenge for mass spectrometry based method can be that mass spectrometer by itself lacks the capability to detect the low concentration of HCPs when mixed with overwhelmed highly concentrated antibody drug substance. To overcome the issue of wide dynamic range (over 6 order of magnitude) between low ppm level HCPs and high abundance therapeutic antibody, one strategy is to resolve the co-eluting peptides before mass spectrometry analysis, by adding another dimension of separation such as 2D-LC and ion mobility on the top of data-dependent acquisition or data-independent acquisition to increase the separation efficiency. In one study, Ecker et al. reported the single digit ppm level HCPs identification using LC-MS/MS with data independent acquisition and they also established a library including masses, retention times and fragment ions for the HCPs from null strains. Although this method is sensitive, this method may lose the HCPs that are only co-expressed with certain product (Dawn M Ecker, Susan Dana Jones & Howard L Levine, *The therapeutic monoclonal antibody market*, 7 MABS 9-14 (2014)). Another study showed the capability of identifying 10 to 50 ppm HCPs using 2D-HPLC with ion mobility (Catalin Doneanu et al., *Analysis of host-cell proteins in biotherapeutic proteins by comprehensive online two-dimensional liquid chromatography/mass spectrometry*, 4 MABS 24-44 (2012)). However, the cycle times of 2D-LC are very long, and this method is not sensitive enough for lower level of HCPs (<10 ppm) analysis. The other strategies focus on sample preparation to enrich HCPs by removing antibody in sample with affinity purification, limited digestion or by capturing HCPs using polyclonal antibodies (Lihua Huang et al., *A Novel Sample Preparation for Shotgun Proteomics Characterization of HCPs in Antibodies*, 89 ANALYTICAL CHEMISTRY 5436-5444 (2017); Jenny Heidbrink Thompson et al., *Improved detection of host cell proteins (HCPs) in a mammalian cell-derived antibody drug using liquid chromatography/mass spectrometry in conjunction with an HCP-enrichment strategy*, 28 RAPID COMMUNICATIONS IN MASS SPECTROMETRY 855-860 (2014); James A Madsen et al., *Toward the complete characterization of host cell proteins in biotherapeutics via affinity depletions, LC-MS/MS, and multivariate analysis*, 7 MABS 1128-1137 (2015)).

One of the major challenge for the existing methods can be a lack of capability to detect low concentration of HCPs in a sample (for example, 0.01-10 ppm) with a wide dynamic range (5-8 order) between HCP and drug which can cause the HCP signal to get masked in the analysis.

Considering the limitations of existing methods, an effective and efficient method for identification of HCPs was developed.

Unless described otherwise, all technical and scientific terms used herein have the same meaning as commonly understood by one of ordinary skill in the art to which this invention belongs. Although any methods and materials similar or equivalent to those described herein can be used in the practice or testing, particular methods and materials are now described. All publications mentioned are hereby incorporated by reference.

The term "a" should be understood to mean "at least one"; and the terms "about" and "approximately" should be understood to permit standard variation as would be understood by those of ordinary skill in the art; and where ranges are provided, endpoints are included.

In some exemplary embodiments, the disclosure method for identifying a host-cell protein in a sample matrix.

As used herein, the term "host-cell protein" includes protein derived from the host cell and can be unrelated to the desired protein of interest. Host-cell protein can be a process-related impurity which can be derived from the manufacturing process and can include the three major categories: cell substrate-derived, cell culture-derived and downstream derived. Cell substrate-derived impurities include, but are not limited to, proteins derived from the host organism and nucleic acid (host cell genomic, vector, or total DNA). Cell culture-derived impurities include, but are not limited to, inducers, antibiotics, serum, and other media components. Downstream-derived impurities include, but are not limited to, enzymes, chemical and biochemical processing reagents (e.g., cyanogen bromide, guanidine, oxidizing and reducing agents), inorganic salts (e.g., heavy metals, arsenic, nonmetallic ion), solvents, carriers, ligands (e.g., monoclonal antibodies), and other leachables.

During manufacturing of a protein using cell-based systems, the product itself must be purified from any cell-based impurities to an acceptable level before use. The impurities that may be derived from expression systems, whereby not only is the protein of interest secreted into the cell culture fluid that is collected for harvest, but host cell protein(s) (HCPs), nucleic acids, lipids, and other cellular material that may be released into the culture media along with product impurities (See Bracewell, supra). HCPs in particular, must be monitored and in the final product as they might be unacceptable for a particular HCP in terms of risk or product degradation or lead to the development of immunogenic forms of the product. The downstream processing can use separations to separate a protein of interest from the diverse spectrum of HCPs.

In some exemplary embodiments, the sample matrix can comprise a protein of interest.

As used herein, the term "protein of interest" includes any amino acid polymer having covalently linked amide bonds.

Proteins comprise one or more amino acid polymer chains, generally known in the art as "polypeptides". "Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. "Synthetic peptides or polypeptides" refers to a non-naturally occurring peptide or polypeptide. Synthetic peptides or polypeptides can be synthesized, for example, using an automated polypeptide synthesizer. Various solid phase peptide synthesis methods are known to those of skill in the art. A protein may contain one or multiple polypeptides to form a single functioning biomolecule. A protein can include any of bio-therapeutic proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. In another exemplary aspect, a protein can include antibody fragments, nanobodies, recombinant antibody chimeras, cytokines, chemokines, peptide hormones, and the like. Proteins may be produced using recombinant cell-based production systems, such as the insect baculovirus system, yeast systems (e.g., Pichia sp.), mammalian systems (e.g., CHO cells and CHO derivatives like CHO-K1 cells). For a review discussing biotherapeutic proteins and their production, see Ghaderi et al., "Production platforms for biotherapeutic glycoproteins. Occurrence, impact, and challenges of non-human sialylation," (BIOTECHNOL. GENET. ENG. REV. 147-175 (2012)). In some exemplary embodiments, proteins comprise modifications, adducts, and other covalently linked moieties. Those modifications, adducts and moieties include for example avidin, streptavidin, biotin, glycans (e.g., N-acetylgalactosamine, galactose, neuraminic acid, N-acetylglucosamine, fucose, mannose, and other monosaccharides), PEG, polyhistidine, FLAGtag, maltose binding protein (MBP), chitin binding protein (CBP), glutathione-S-transferase (GST) myc-epitope, fluorescent labels and other dyes, and the like. Proteins can be classified on the basis of compositions and solubility and can thus include simple proteins, such as, globular proteins and fibrous proteins; conjugated proteins, such as, nucleoproteins, glycoproteins, mucoproteins, chromoproteins, phosphoproteins, metalloproteins, and lipoproteins; and derived proteins, such as, primary derived proteins and secondary derived proteins.

In some exemplary embodiments, the protein of interest can be an antibody, a bispecific antibody, a multispecific antibody, antibody fragment, monoclonal antibody, host-cell protein or combinations thereof.

The term "antibody," as used herein includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_{H2}$ and $C_H3$. Each light chain comprises a light chain variable region (abbreviated herein as LCVR or $V_L$) and a light chain constant region. The light chain constant region comprises one domain (C.sub.L1). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different exemplary embodiments, the FRs of the anti-big-ET-1 antibody (or antigen-binding portion thereof) may be identical to the human germline sequences, or may be naturally or artificially modified. An amino acid consensus sequence may be defined based on a side-by-side analysis of two or more CDRs. The term "antibody," as used herein, also includes antigen-binding fragments of full antibody molecules.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a Fc fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. An antibody fragment may be produced by various means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multi-molecular complex.

The term "monoclonal antibody" as used herein is not limited to antibodies produced through hybridoma technology. A monoclonal antibody can be derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

In a particular aspect, the protein of interest is selected from the group consisting of aflibercept, recombinant Mini-Trap (examples of which are disclosed in U.S. Pat. No.

7,279,159), a scFv and other anti-VEGF proteins. In a preferred aspect, the recombinant protein of interest is aflibercept.

In some exemplary embodiments, the sample matrix can optionally comprise product-related impurities.

As used herein, "product-related impurities" (e.g., precursors, certain degradation products) can be molecular variants arising during manufacture and/or storage that do not have properties comparable to those of the desired product with respect to activity, efficacy, and safety. Such variants may need considerable effort in isolation and characterization in order to identify the type of modification(s). Product-related impurities can include truncated forms, modified forms, and aggregates. Truncated forms are formed by hydrolytic enzymes or chemicals which catalyze the cleavage of peptide bonds. Modified forms include, but are not limited to, deamidated, isomerized, mismatched S-S linked, oxidized, or altered conjugated forms (e.g., glycosylation, phosphorylation). Modified forms can also include any post-translational modification form. Aggregates include dimers and higher multiples of the desired product. (Q6B Specifications: Test Procedures and Acceptance Criteria for Biotechnological/Biological Products, ICH August 1999, U.S. Dept. of Health and Humans Services).

In some exemplary embodiments, the sample matrix can be a protein formulation.

As used herein, the term "protein formulation" refers to a therapeutic protein that is formulated together with one or more pharmaceutically acceptable vehicles. In some embodiments, the therapeutic protein is present in a unit dose amount appropriate for administration in a therapeutic regimen. In some exemplary embodiments, the formulation can further comprise excipients including, but not limited to buffering agents, bulking agents, tonicity modifiers, surfactants, solubilizing agents, and preservatives. Other additional excipients can also be selected based on function and compatibility with the formulations may be found, for example in Loyd V. Allen, REMINGTON: THE SCIENCE AND PRACTICE OF PHARMACY (19 ed. 1995), John E Hoover, REMINGTON'S PHARMACEUTICAL SCIENCES (1975), and Lyod Allen, ANSEL'S PHARMACEUTICAL DOSAGE FORMS AND DRUG DELIVERY SYSTEMS (10 ed.) herein incorporated by reference in their entirety.

In some exemplary embodiments, the method of identifying a host-cell protein in a sample matrix having a protein of interest can comprise dissociating a host-cell protein from a protein of interest. Dissociating a host-cell protein from a protein of interest can be carried out using a protein dissociating agent. Non-limiting examples of a protein dissociating agent include heat, high or low pH, or exposure to chaotropic agents. Several chaotropic agents can be used as protein dissociating agents. Chaotropic solutes increase the entropy of the system by interfering with intramolecular interactions mediated by non-covalent forces such as hydrogen bonds, van der Waals forces, and hydrophobic effects. Non-limiting examples for chaotropic agents include butanol, ethanol, guanidinium chloride, lithium perchlorate, lithium acetate, magnesium chloride, phenol, propanol, sodium dodecyl sulfate, thiourea, N-lauroylsarcosine, urea, and salts thereof. In one aspect, dissociating a host-cell protein from a protein of interest can comprise denaturing the protein of interest. In another aspect, dissociating a host-cell protein from a protein of interest can comprise denaturing the host-cell protein. As used herein, the term "denaturing" refers to a process in which the three-dimensional shape of a molecule is changed from its native state without rupture of peptide bonds.

In some exemplary embodiments, the method of identifying a host-cell protein in a sample matrix having a protein of interest can comprise filtering a dissociated host-cell protein using a molecular weight cut-off filter.

As used herein, the term "molecular weight cut-off filter" can include filters or membranes or filtration methods that can have an ability to retain at least about 90% solute or a protein of a known molecular weight (KDa). In some exemplary embodiments, the molecular weight cut-off filter can have a cut-off of at least about 30 KDa. In some other exemplary embodiments, the molecular weight cut-off filter can have a cut-off of at least about 50 KDa. In some further exemplary embodiments, the molecular weight cut-off filter can have a cut-off of at least about 100 KDa. Molecular weight cut-off filters can be available from several commercial suppliers, for example Microcon, Millipore, Centrisart, Sartorius, Amicon Ultra, Millipore, Vivaspin, and Sartorius. The molecular weight cut-off filter can be selected on the basis of molecular weight cut-off required, operating conditions, concentration of the filtered sample or composition of the filtered sample. In some exemplary embodiments, the method of identifying a host-cell protein in a sample matrix can comprise contacting a host-cell protein to a hydrolyzing agent.

In some exemplary embodiments, the method of identifying a host-cell protein in a sample matrix having a protein of interest can comprise dissociating a host-cell protein from a protein of interest, filtering the dissociated host-cell protein using a molecular weight cut-off filter and contacting the filtered host-cell protein to a hydrolyzing agent.

As used herein, the term "hydrolyzing agent" refers to any one or combination of a large number of different agents that can perform digestion of a protein. Non-limiting examples of hydrolyzing agents that can carry out enzymatic digestion include trypsin, endoproteinase Arg-C, endoproteinase Asp-N, endoproteinase Glu-C, outer membrane protease T (OmpT), immunoglobulin-degrading enzyme of *Streptococcus pyogenes* (IdeS), chymotrypsin, pepsin, thermolysin, papain, pronase, and protease from *Aspergillus saitoi*. Non-limiting examples of hydrolyzing agents that can carry out non-enzymatic digestion include the use of high temperature, microwave, ultrasound, high pressure, infrared, solvents (non-limiting examples are ethanol and acetonitrile), immobilized enzyme digestion (IMER), magnetic particle immobilized enzymes, and on-chip immobilized enzymes. For a recent review discussing the available techniques for protein digestion see Switazar et al., "Protein Digestion: An Overview of the Available Techniques and Recent Developments" (Linda Switzar, Martin Giera & Wilfried M. A. Niessen, *Protein Digestion: An Overview of the Available Techniques and Recent Developments,* 12 JOURNAL OF PROTEOME RESEARCH 1067-1077 (2013)). One or a combination of hydrolyzing agents can cleave peptide bonds in a protein or polypeptide, in a sequence-specific manner, generating a predictable collection of shorter peptides.

The term ratio of hydrolyzing agent to the protein and the time required for digestion can be appropriately selected to obtain a digestion of the protein. When the enzyme to substrate ratio is unsuitably high, the correspondingly high digestion rate will not allow sufficient time for the peptides to be analyzed by mass spectrometer, and sequence coverage will be compromised. On the other hand, a low E/S ratio would need long digestion and thus long data acquisition time. The enzyme to substrate ratio can range from about 1:0.5 to about 1:200. As used herein, the term "digestion" refers to hydrolysis of one or more peptide bonds of a protein. There are several approaches to carrying out digestion of a protein in a sample using an appropriate hydrolyzing agent, for example, enzymatic digestion or non-enzymatic digestion.

One of the widely accepted methods for digestion of proteins in a sample involves the use of proteases. Many proteases are available and each of them have their own characteristics in terms of specificity, efficiency, and optimum digestion conditions. Proteases refer to both endopeptidases and exopeptidases, as classified based on the ability of the protease to cleave at non-terminal or terminal amino acids within a peptide. Alternatively, proteases also refer to the six distinct classes—aspartic, glutamic, and metalloproteases, cysteine, serine, and threonine proteases, as classified on the mechanism of catalysis. The terms "protease" and "peptidase" are used interchangeably to refer to enzymes which hydrolyze peptide bonds.

Apart from contacting a host-cell protein to a hydrolyzing agent, the method can optionally include steps for reducing the host-cell protein, alkylating the host-cell protein, buffering the host-cell protein, and/or desalting the sample matrix. These steps can be accomplished in any suitable manner as desired.

In some exemplary embodiments, the method of identifying a host-cell protein in a sample matrix can optionally comprise contacting a host-cell protein to a protein reducing agent.

As used herein, the term "protein reducing agent" refers to the agent used for reduction of disulfide bridges in a protein. Non-limiting examples of the protein reducing agents used to reduce the protein are dithiothreitol (DTT), β-mercaptoethanol, Ellman's reagent, hydroxylamine hydrochloride, sodium cyanoborohydride, tris(2-carboxyethyl)phosphine hydrochloride (TCEP-HCl), or combinations thereof.

In some exemplary embodiments, the method of identifying a host-cell protein in a sample matrix can optionally comprise contacting a host-cell protein to a protein alkylating agent.

As used herein, the term "protein alkylating agent" refers to the agent used for alkylate certain free amino acid residues in a protein. Non-limiting examples of the protein alkylating agents are iodoacetamide (IOA), chloroacetamide (CAA), acrylamide (AA), N-ethylmaleimide (NEM), methyl methanethiosulfonate (MMTS), and 4-vinylpyridine or combinations thereof.

In some exemplary embodiments, the method of identifying a host-cell protein in a sample matrix having a protein of interest can comprise dissociating a host-cell protein from a protein of interest, filtering the dissociated host-cell protein using a molecular weight cut-off filter and identifying the host-cell protein using a bottom-up or shotgun proteomics approach.

In a conventional bottom-up approach experiment, a protein can be digested into small polypeptides to be characterized. The peptide mixture can be then subjected to mass spectrometry analysis. Peptide identification can be further performed by comparing the mass spectra derived from the polypeptide fragmentation with the theoretical mass spectra generated from in silico digestion of a protein. Protein inference is then accomplished by assigning peptide sequence to proteins.

A common peptide mapping workflow can comprise steps for protein denaturation, reduction and alkylation of cysteine residues, proteolytic digestion, and liquid chromatography coupled with tandem mass spectrometry (LC-MS/MS) analysis (Pavel V. Bondarenko et al., Mass measurement and top-down HPLC/MS analysis of intact monoclonal antibodies on a hybrid linear quadrupole ion trap-orbitrap mass spectrometer, 20 JOURNAL OF THE AMERICAN SOCIETY FOR MASS SPECTROMETRY 1415-1424 (2009); James Bourell et al., Electrospray Ionization Mass Spectrometry of Recombinantly Engineered Antibody Fragments, 66 ANALYTICAL CHEMISTRY 2088-2095 (1994); Wei Zhang et al., Complete disulfide bond assignment of a recombinant immunoglobulin G4 monoclonal antibody, 311 ANALYTICAL BIOCHEMISTRY 1-9 (2002); Daniel S. Kroon et al., Rapid profiling of carbohydrate glycoforms in monoclonal antibodies using MALDI/TOF mass spectrometry, 13 JOURNAL OF PHARMACEUTICAL AND BIOMEDICAL ANALYSIS 1049-1054 (1995) B. W. Gibson & K. Biemann, Strategy for the mass spectrometric verification and correction of the primary structures of proteins deduced from their DNA sequences., 81 PROCEEDINGS OF THE NATIONAL ACADEMY OF SCIENCES 1956-1960 (1984); Dirk Chelius, Douglas S. Rehder & Pavel V. Bondarenko, Identification and Characterization of Deamidation Sites in the Conserved Regions of Human Immunoglobulin Gamma Antibodies, 77 ANALYTICAL CHEMISTRY 6004-6011 (2005); Neil Kelleher, Top-down proteomics; 76 ANALYTICAL CHEMISTRY 197A-203A (2004); Yuan Mao et al., Top-Down Structural Analysis of an Intact Monoclonal Antibody b Electron Capture Dissociation-Fourier Transform Ion Cyclotron Resonance-Mass Spectrometry, 85 ANALYTICAL CHEMISTRY 4239-4246 (2013); Yury O Tsybin et al, Structural Analysis of Intact Monoclonal Antibodies by Electron Transfer Dissociation Mass Spectrometry, 83 ANALYTICAL CHEMISTRY 8919-8927 (2011); Luca Fornelli et al., Analysis of Intact Monoclonal Antibody IgG1 by Electron Transfer Dissociation Orbitrap FTMS, 11 MOLECULAR & CELLULAR PROTEOMICS 1758-1767 (2012), Catherine. A. Srebalus Barnes & Amareth Lim, Applications of mass spectrometry for the structural characterization of recombinant protein pharmaceuticals, 26 MASS SPECTROMETRY REVIEWS 370-388 (2007)). Due to the rapid advancements in liquid chromatography and mass spectrometry instrumentation, this peptide mapping method can now routinely generate almost complete sequence coverage, and thus has become an effective approach for confirming monoclonal antibody identity.

In some exemplary embodiments, the method of identifying a host-cell protein in a sample matrix having a protein of interest can comprise dissociating a host-cell protein from a protein of interest, filtering the host-cell protein using a molecular weight cut-off filter and identifying the host-cell protein using a mass-spectrometer.

As used herein, the term "mass spectrometer" includes a device capable of identifying specific molecular species and measuring their accurate masses. The term is meant to include any molecular detector into which a polypeptide or peptide may be eluted for detection and/or characterization. A mass spectrometer can include three major parts: the ion source, the mass analyzer, and the detector. The role of the ion source is to create gas phase ions. Analyte atoms, molecules, or clusters can be transferred into gas phase and ionized either concurrently (as in electrospray ionization) or through separate processes. The choice of ion source depends heavily on the application.

In some exemplary embodiments, the mass spectrometer can be a tandem mass spectrometer.

As used herein, the term "tandem mass spectrometry" includes a technique where structural information on sample molecules is obtained by using multiple stages of mass selection and mass separation. A prerequisite is that the sample molecules can be transferred into gas phase and ionized intact and that they can be induced to fall apart in some predictable and controllable fashion after the first mass selection step. Multistage MS/MS, or MS$^n$, can be performed by first selecting and isolating a precursor ion (MS$^2$), fragmenting it, isolating a primary fragment ion (MS$^3$), fragmenting it, isolating a secondary fragment (MS$^4$), and so on as long as one can obtain meaningful information as the fragment ion signal is detectable. Tandem MS has been successfully performed with a wide variety of analyzer combinations. What analyzers to combine for a certain application can be determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers. A tandem-in-space mass spectrometer comprises an ion source, a precursor ion activation device, and at least two non-trapping mass analyzers. Specific m/z separation functions can be designed so that in one section of the instrument ions are selected, dissociated in an intermediate region, and the product ions are then transmitted to another analyzer for m/z separation and data acquisition. In tandem-in-time, mass spectrometer ions produced in the ion source can be trapped, isolated, fragmented, and m/z separated in the same physical device.

The peptides identified by the mass spectrometer can be used as surrogate representatives of the intact protein and their post translational modifications. They can be used for protein characterization by correlating experimental and theoretical MS/MS data, the latter generated from possible peptides in a protein sequence database. The characterization includes, but is not limited to, sequencing amino acids of the protein fragments, determining protein sequencing, determining protein de novo sequencing, locating post-translational modifications, or identifying post translational modifications, or comparability analysis, or combinations thereof.

As used herein, the term "database" refers to bioinformatic tools which provide the possibility of searching the uninterpreted MS-MS spectra against all possible sequences in the database(s). Non-limiting examples of such tools are Mascot (http://www.matrixscience.com), Spectrum Mill (http://www.chem.agilent.com), PLGS (http://www.waters.com), PEAKS (http://www.bioinformaticssolutions.com), Proteinpilot (http://download.appliedbiosystems.com//proteinpilot), Phenyx (http://www.phenyx-ms.com), Sorcerer (http://www.sagenresearch.com), OMS SA (http://www-.pubchem.ncbi.nlm.nih.gov/omssa/), X!Tandem (http://www.thegpm.org/TANDEM/), Protein Prospector (http://www.http://prospector.ucsf.edu/prospector/mshome.htm), Byonic (https://www.proteinmetrics.com/products/byonic) or Sequest (http://fields scripps.edu/sequest).

In some exemplary embodiments, the mass spectrometer can be coupled to a liquid chromatography system.

As used herein, the term "chromatography" refers to a process in which a chemical mixture carried by a liquid or gas can be separated into components as a result of differential distribution of the chemical entities as they flow around or over a stationary liquid or solid phase. Non-limiting examples of chromatography include traditional reversed-phased (RP), ion exchange (IEX) and normal phase chromatography (NP). Unlike RP, NP and IEX chromatography, in which hydrophobic interaction, hydrophilic interaction and ionic interaction respectively are the dominant interaction modes, mixed-mode chromatography can employ a combination of two or more of these interaction modes. Several types of liquid chromatography can be used with the mass spectrometer, such as, rapid resolution liquid chromatography (RRLC), ultra performance liquid chromatography (UPLC), ultra-fast liquid chromatography (UFLC) and nano liquid chromatography (nLC). For further details on chromatography method and principles, see Colin et al. (Colin F. Poole et al., LIQUID CHROMATOGRAPHY FUNDAMENTALS AND INSTRUMENTATION (2017)).

In some exemplary embodiments, the method of identifying a host-cell protein in a sample matrix can comprise identifying the host-cell protein using a top-down proteomics approach.

In some exemplary embodiments, the method of identifying a host-cell protein in a sample matrix can comprise identifying the host-cell protein using native-MS.

In the top-down proteomics approach, intact proteins can be analyzed. The top-down MS can provide comprehensive sequence information for the whole protein by detecting all types of PTMs (e.g. phosphorylation, proteolysis, acetylation) and sequence variants (e.g. mutations, polymorphisms, alternatively spliced isoforms) simultaneously in one spectrum (a "bird's eye view") without a priori knowledge (Neil L. Kelleher et al., *Top Down versus Bottom Up Protein Characterization by Tandem High-Resolution Mass Spectrometry*, 121 JOURNAL OF THE AMERICAN CHEMICAL SOCIETY 806-812 (1999); B. T. Chait, *CHEMISTRY: Mass Spectrometry: Bottom-Up or Top-Down?*, 314 SCIENCE 65-66 (2006); Zachery R. Gregorich & Ying Ge, *Top-down proteomics in health and disease: Challenges and opportunities*, 14 PROTEOMICS 1195-1210 (2014)).

In some exemplary embodiments, the host-cell protein can have a pI in the range of about 4.5 to about 9.0. In one exemplary specific embodiment, the pI can be about 4.5, about 5.0, about 5.5, about 5.6, about 5.7, about 5.8, about 5.9, about 6.0, about 6.1 about 6.2, about 6.3, about 6.4, about 6.5, about 6.6, about 6.7, about 6.8, about 6.9, about 7.0, about 7.1 about 7.2, about 7.3, about 7.4, about 7.5, about 7.6, about 7.7, about 7.8, about 7.9, about 8.0, about 8.1 about 8.2, about 8.3, about 8.4, about 8.5, about 8.6, about 8.7, about 8.8, about 8.9, or about 9.0.

In some exemplary embodiments, the types of host-cell proteins in the sample matrix can be at least two.

In some exemplary embodiments, the concentration of the host-cell proteins in the sample matrix can be lower than about from 0.05 ppm. In some specific exemplary embodiments, the concentration of the host-cell proteins in the sample matrix can be lower than about 0.05 ppm, lower than about 1 ppm, lower than about 2 ppm, lower than about 3 ppm, lower than about 4 ppm, lower than about 5 ppm, lower than about 10 ppm, lower than about 20 ppm, lower than about 30 ppm, lower than about 40 ppm, lower than about 50 ppm, lower than about 60 ppm, lower than about 70 ppm, lower than about 80 ppm, lower than about 90 ppm, lower than about 100 ppm, lower than about 150 ppm, lower than about 200 ppm, lower than about 250 ppm, lower than about 300 ppm, lower than about 350 ppm, lower than about 400 ppm, lower than about 450 ppm, lower than about 500 ppm, lower than about 550 ppm, lower than about 600 ppm, lower than about 650 ppm, lower than about 700 ppm, lower than about 750 ppm, lower than about 800 ppm, lower than about 850 ppm, lower than about 900 ppm, lower than about 950 ppm, or lower than about 1000 ppm.

In another exemplary embodiment, the sample matrix can be obtained from any step of the bioprocess, such as, culture cell culture fluid (CCF), harvested cell culture fluid (HCCF), process performance qualification (PPQ), any step in the downstream processing, drug solution (DS), or a drug product (DP) comprising the final formulated product. In some other specific exemplary embodiments, the sample can be selected from any step of the downstream process of clarification, chromatographic purification, viral inactivation, or filtration. In some specific exemplary embodiments, the drug product can be selected from manufactured drug product in the clinic, shipping, storage, or handling.

In some exemplary embodiments, the method for identifying host-cell protein(s) in a sample matrix having a protein of interest can comprise dissociating a host-cell protein from a protein of interest using N-lauroylsarcosine or sodium deoxycholate or both at a suitable temperature.

In some exemplary embodiments, the host-cell protein can be dissociated by exposing the host-cell protein to an acidic or basic pH. In some exemplary embodiments the host-cell protein can be dissociated by exposing the host-cell protein to an acidic pH, for example, at a the pH of about 0, or about 0.5, or about 1, or about 1.5, or about 2, or about 2.5, or about 3, or about 3.5, or about 4, or about 4.5, or about 5, or about 5.5, or about 6. In one exemplary embodiment, the host-cell protein can be dissociated by exposing the host-cell protein to a basic pH, for example, at a pH of about 8, or about 8.5, or about 9, or about 9.5, or about 10, or about 10.5, or about 11, or about 11.5, or about 12, or about 12.5, or about 13, or about 13.5, or about 14.

In some exemplary embodiments, the method for identifying host-cell protein(s) in a sample matrix can comprise alkylating a host-cell protein.

In some exemplary embodiments, the method for identifying host-cell protein(s) in a sample matrix can optionally comprise a step of desalting a solution having the host-cell protein. Desalting can be performed by using dialysis, ultrafiltration, desalting chromatography columns, gel filtration column, centrifugal ultra-filtration, or combinations thereof.

In some exemplary embodiments, the method can further comprise digesting the sample under dissociating conditions. In some specific exemplary embodiments, the sample can be digested using a hydrolyzing agent, wherein the hydrolyzing agent can be selected from protease from *Aspergillus Saitoi*, elastase, subtilisin, protease XIII, pepsin, trypsin, Tryp-N, chymotrypsin, aspergillopepsin I, LysN protease (Lys-N), LysC endoproteinase (Lys-C), endoproteinase Asp-N (Asp-N), endoproteinase Arg-C (Arg-C), endoproteinase Glu-C (Glu-C) or outer membrane protein T (OmpT), immunoglobulin-degrading enzyme of *Streptococcus pyogenes* (IdeS), thermolysin, papain, pronase, V8 protease or biologically active fragments or homologs thereof or combinations thereof. In some exemplary embodiments, the concentration of the solution containing hydrolyzing agent can be about 0.1 µg/µL to about 100 µg/µL. In one embodiment, the concentration of the solution can be about 0.1 µg/µL, or about 0.2 µg/µL, or 0.5 µg/µL, or about 1 µg/µL, or about 2 µg/µL, or about 3 µg/µL, or about 4 µg/µL, or about 5 µg/µL, or about 10 µg/µL, or about 15 µg/µL, or about 20 µg/µL, or about 25 µg/µL, or about 30 µg/µL, or about 35 µg/µL, or about 40 µg/µL, or about 45 µg/µL, or about 50 µg/µL, or about 60 µg/µL, or about 70 µg/µL, or about 80 µg/µL, or about 90 µg/µL, or about 100 µg/µL. The concentration of the protein in a sample can range from about 0.1 µg/µL to about 100 µg/µL. In some exemplary embodiments, wherein the weight ratio of hydrolyzing agent to the host-cell protein can range from about 1:0.1 to about 1:50. For example, the ratio of hydrolyzing agent to the host-cell protein (w/w) can be about 1:0.5, or about 1:1, or about 1:2, or about 1:3, or about 1:4, or about 1:5, or about 1:10, or about 1:15, or about 1:20, or about 1:25, or about 1:30, or about 1:35, or about 1:40, or about 1:45, or about 1:50.

In some exemplary embodiments, the method for identifying host-cell protein(s) in a sample matrix can comprise filtering a host-cell protein using a molecular weight cut-off filter. In some specific exemplary embodiments, the filtered host-cell protein can be filtered with dissociating. In some other specific exemplary embodiments, the filtered host-cell protein can be filtered without dissociating.

In some exemplary embodiments, the molecular weight filter of the molecular weight cut-off filter can be greater than about 30 KDa. In some specific exemplary embodiments, the molecular weight filter of the molecular weight cut-off filter can be greater than about 30 KDa, greater than about 35 KDa, greater than about 40 KDa, greater than about 45 KDa, greater than about 50 KDa, greater than about 55 KDa, greater than about 60 KDa, greater than about 65 KDa, greater than about 70 KDa, greater than about 75 KDa, greater than about 80 KDa, greater than about 85 KDa, greater than about 90 KDa, greater than about 95 KDa, greater than about 100 KDa, greater than about 110 KDa, greater than about 120 KDa, greater than about 130 KDa, greater than about 140 KDa, greater than about 150 KDa, greater than about 160 KDa, greater than about 170 KDa, greater than about 180 KDa, greater than about 190 KDa, greater than about 200 KDa.

In some exemplary embodiments, filtering the host-cell protein using a molecular weight cut-off filter enriches the host-cell protein at least about 5-fold. In some specific exemplary embodiments, the enrichment of the host-cell protein by at least about 5-fold, at least about 10-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, at least about 100-fold, at least about 105-fold, at least about 110-fold, at least about 115-fold, at least about 120-fold, at least about 125-fold, at least about 130-fold, at least about 135-fold, at least about 140-fold, at least about 145-fold, at least about 150-fold, at least about 155-fold, at least about 160-fold, at least about 165-fold, at least about 170-fold, at least about 175-fold, at least about 180-fold, at least about 185-fold, at least about 190-fold, at least about 195-fold, or at least about 200-fold.

In some exemplary embodiments, the method for identifying host-cell protein(s) in a sample matrix can comprise identifying the host-cell protein using a mass spectrometer.

In some exemplary embodiments, an ion source for the mass spectrometer can be an electrospray infusion setup. In some other exemplary embodiments, a mass analyzer for the mass analyzer can be selected from time-of-flight (TOF), magnetic/electric sector, quadrupole mass filter (Q), quadrupole ion trap (QIT), orbitrap, Fourier transform ion cyclotron resonance (FTICR), accelerator mass spectrometry (AMS), or combinations thereof. In one exemplary embodiment, the electrospray infusion setup can be on-line with the mass spectrometer. The electrospray infusion setup may include an electrospray emitter, nebulization gas, and/or an ESI power supply. The electrospray emitter can have a carbon-coated infusion tip. The ESI power supply can apply a positive/negative voltage on the carbon-coated infusion tip of the electrospray emitter while the mass spectrometer sample orifice remains at 0 kV, generating an intense electrostatic field between the final sample in the emitter and the grounded orifice of the mass spectrometer and hence generates the electrospray. In one exemplary embodiment, a positive voltage can be applied on the carbon-coated infusion tip of the electrospray emitter. The positive voltage applied on the carbon-coated infusion tip of the electrospray emitter can be selected from about 0.5 kV, about 1 kV, about 1.4 kV, about 2 kV, about 3 kV, or about 4 kV.

In some exemplary embodiments, the mass spectrometer can be coupled to a liquid chromatography. In some specific exemplary embodiments, the mass spectrometer can be coupled to a nano liquid chromatography. In some exemplary embodiments, the mobile phase used to elute the protein in liquid chromatography can be a mobile phase that can be compatible with a mass spectrometer. In some specific exemplary embodiments, the mobile phase can be ammonium acetate, ammonium bicarbonate, or ammonium formate, or combinations thereof.

In another exemplary embodiment, the mass spectrometer can comprise a nanospray.

In some exemplary embodiments, the mass spectrometer can be a tandem mass spectrometer to characterize the protein.

In some exemplary embodiments, the detection limit of the method can be at least about 0.5 ppm. In some specific exemplary embodiments, the detection limit can be lower than at least about 0.5 ppm, lower than at least about 1 ppm, lower than at least about 2 ppm, lower than at least about 3 ppm, lower than at least about 4 ppm, lower than at least about 5 ppm, lower than [at least about 10 ppm, lower than at least about 20 ppm, lower than at least about 30 ppm, lower than at least about 40 ppm, lower than at least about 50 ppm, lower than at least about 60 ppm, lower than at least about 70 ppm, lower than at least about 80 ppm, lower than at least about 90 ppm, lower than at least about 100 ppm, lower than at least about 150 ppm, lower than at least?] about 200 ppm, lower than at least about 250 ppm, lower than at least about 300 ppm, lower than at least about 350 ppm, lower than at least about 400 ppm, lower than at least about 450 ppm, lower than at least about 500 ppm, lower than at least about 550 ppm, lower than at least about 600 ppm, lower than at least about 650 ppm, lower than at least about 700 ppm, lower than at least about 750 ppm, lower than at least about 800 ppm, lower than at least about 850 ppm, lower than at least about 900 ppm, lower than at least about 950 ppm, or lower than at least about 1000 ppm.

In some exemplary embodiments, the method comprising steps for filtering a host-cell protein using a molecular weight cut-off filter can have at least about 5-fold higher detection limit than a method not comprising a step for filtering a host-cell protein using a molecular weight cut-off filter. In some specific exemplary embodiments, the detection limit can be higher by at least about 5-fold, at least about 10-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, at least about 100-fold, at least about 105-fold, at least about 110-fold, at least about 115-fold, at least about 120-fold, at least about 125-fold, at least about 130-fold, at least about 135-fold, at least about 140-fold, at least about 145-fold, at least about 150-fold, at least about 155-fold, at least about 160-fold, at least about 165-fold, at least about 170-fold, at least about 175-fold, at least about 180-fold, at least about 185-fold, at least about 190-fold, at least about 195-fold, or at least about 200-fold.

It is understood that the present invention is not limited to any of the aforesaid host-cell protein(s), hydrolyzing agent(s), protein dissociating agent(s), protein alkylating agent(s), instrument(s) used for identification, and molecular weight cut-off filter(s), and that any host-cell protein(s), hydrolyzing agent(s), protein dissociating agent(s), protein alkylating agent(s), instrument(s) used for identification, and molecular weight cut-off filter(s) can be selected by any suitable means.

The consecutive labeling of method steps as provided herein with numbers and/or letters is not meant to limit the method or any embodiments thereof to the particular indicated order.

Various publications, including patents, patent applications, published patent applications, accession numbers, technical articles and scholarly articles are cited throughout the specification. Each of these cited references is herein incorporated by reference, in its entirety and for all purposes.

The disclosure will be more fully understood by reference to the following Examples, which are provided to describe the disclosure in greater detail. They are intended to illustrate and should not be construed as limiting the scope of the disclosure.

EXAMPLES

Material. All chemicals were of high purity and were obtained from commercial sources. LC-MS grade chromatography solvents were purchased from Thermo Fisher Scientific. Monoclonal antibody (mAb1, hereafter) and spiked in CHO proteins were produced by Regeneron (Tarrytown, NY). Sodium deoxycholate (SDC) and sodium lauroyl sarcosinate (SLS) and chloroacetamide (CAA) were purchased from Sigma-Aldrich (St. Louis MO). Tris-(2-carboxyethyl) phosphine (TCEP) was purchased from Thermo Fisher Scientific. NIST monoclonal antibody standard RM 8670 was from National Institute of Standards and Technology.

Sample preparation and protein digestion. The therapeutic antibody was solubilized in 100 μl of denature buffer containing 12 mM SDC and 12 mM SLS in 100 mM Tris-HCl, pH 8.0. The denatured proteins were loaded into Amicon μltra-0.5, 50 KDa filter (Millipore sigma), then centrifuged at 13,000 rpm for 8 minutes to obtain antibody depleted sample from the collection tube. The antibody depleted sample were reduced and alkylated with 10 mM TCEP and 40 mM CAA at 95° C. for 5 min. Alkylated proteins were diluted to 5 fold by 100 mM Tris-HCl, pH8.0 and digested in a 1:20 (w/w) enzyme-to-protein ratio for overnight at 37° C. The digested peptides were acidified with trifluoroacetic acid (TFA) to final concentration of 1% TFA, and 500 μl of Ethyl acetate was added to 500 μl digested solution. The mixture was shaken for 2 min, then centrifuged at 13,200 rpm for 2 min to obtain aqueous and organic phases. The aqueous phase was collected and dried by speedvac. The dried peptide mixture was resuspended by 0.1% TFA, then desalted using GL-Tip™ SDB desalting tip (GL science, Japan).

NIST standard Direct digestion. The 100 μg of NIST standard was dried with speedvac, then re-constitute with 20 μl of denature/reduction buffer containing 8 M Urea and 10 mM DTT. The proteins were denatured and reduced at 37° C. for 30 minutes, and then incubated with 6 μl of 50 mg/ml iodoacetamide for 30 minutes in dark. Alkylated proteins were digested with 100 μl 0.1 ug/μl trypsin at 37° C. for overnight. The peptide mixture was acidified by 5 μl of 10% TFA. The sample was diluted to 0.4 ug/μl and injected 2 μl for LC-MS/MS analysis.

LC-MS/MS Analysis. The peptide mixture was dissolved in 10 μl of 0.1% formic acid (FA) and inject 8 μl into an μltimate nano LC (Thermo Fisher Scientific). Peptides were separated on a 25 cm column (0.075 mm) C18 column (2.0 um, 100 Å) (Thermo Fisher Scientific). The mobile phase buffer consisted of 0.1% FA in μltra-pure water (Buffer A) and with the eluting buffer of 0.1% FA in 80% ACN (Buffer B) run over with 100 min linear gradient of 2%-25% of buffer B at flow rate of 300 nl/min. The μltimate 3000 nanoLC was coupled with a Q-Exactive HFX mass spectrometer (Thermo Fisher Scientific). The mass spectrometer was operated in the data-dependent mode in where the 10 most intense ions were subjected to higher-energy collisional dissociation (HCD) fragmentation with the normalized collision energy (NCE) 27%, AGC 3e6, max injection time 60 ms) for each full MS scan (from m/z 375-1500 with resolution of 120,000) and AGC 1e5, max injection time 60 ms for MS/MS events (from m/z 200-2000 with resolution of 30,000).

PRM analysis. Samples were dissolved in 8 μL of 0.1% formic acid and 0.5-1 ug of sample were injected into μltimate 3000 nano LC system. Eluent was introduced into the mass spectrometer using 25 cm column (0.075 mm) C18 column (2.0 um, 100 Å). The mobile phase buffer consists of 0.1% formic acid in water with an eluting buffer of 0.1% formic acid (Buffer A) in 80% ACN (Buffer B). The LC flow rate was 300 nl/min. The gradient was set as 2-25% Buffer B for 100 minutes linear gradient. The sample was acquired on Q Exactive HFX (Thermo, Germany). Each sample was analyzed under parallel reaction monitoring (PRM) with an isolation window of 2 m/z. In all experiments, a full mass spectrum at 120,000 resolution relative to m/z 200 (AGC target 1e6, 60 ms maximum injection time, m/z 350-2000) was followed by time scheduled PRM scans at 30,000 resolution (AGC target 1e5, 100 ms maximum injection time). Higher energy collisional dissociation (HCD) was used with 27 eV normalized collision energy.

Therapeutic antibodies are relatively larger molecule compared to HCPs, having a molecular weight of approximately 150 KDa, composed of two parts of polypeptide chain. The separation scheme according to an exemplary embodiment is illustrated in FIG. 1. Sodium deoxycholate and lauroyl sarcosinate cocktail buffer was originally mainly used for membrane protein digestion due to its strong solubility for membrane proteins. (Takeshi Masuda, Masaru Tomita & Yasushi Ishihama, *Phase Transfer Surfactant-Aided Trypsin Digestion for Membrane Proteome Analysis*, 7 JOURNAL OF PROTEOME RESEARCH 731-740 (2008)). This denaturing buffer was adopted in this method not only because it is a strong denaturant, but also it is easy to remove before MS analysis. However, other denaturants can be also used. When applying filtration after denaturation, the majority of antibody would not pass through the filter membrane while most of HCPs would be free to run through the membrane owing to their smaller size. The denatured antibody and its associated HCPs were thus separated based on their molecular size.

Example 1

Filtration efficiency of the selected denaturant was compared with urea in 5% acetic acid, a most commonly used denaturing condition. Before and after filtration, the total protein amount was measured by Nanodrop (Thermo Fisher Scientific). When 1.5 mg antibody sample was passed through a 100K MW cutoff filter with 8 M urea in 5% Acetic acid, the final peptide amount was measured to be 150 μg with no much improvement in total protein identified. With urea as the denaturant, the complexity of the sample was not greatly relieved with only 90% of the protein removal. Given the total HCPs were at less than 100 ppm, the relative antibody level was still at least 3 orders higher than total HCPs. In contrast, the denaturant, SDC+SLS cocktail, greatly improved the filtration efficiency. After SDC+SLS aided filtration, the sample amount was reduced to as low as 4 μg and the number of proteins identified was increase to 26 (Table 1). Assuming that all antibody can be removed by filtration, the proteins left will be HCPs only and the amount should be approximately 0.15 μg. The results suggested that for this particular antibody, there was still good amount of mAb which escaped from 100K MW cutoff membrane, therefore, optimization was needed to further minimize mAb's bypass.

TABLE 1

| Denature Buffer | DS loading amount | Final peptide amount | Total ID | Match to IP's result (confirmed) | High confidence protein No. (>2 peptide) |
|---|---|---|---|---|---|
| 1 8M Urea in 5% AA | 1.5 mg | 150 μg | 83 | 3 | 10 |
| 2 SDC + SLS | 1.5 mg | 4 μg | 124 | 10 | 26 |

Example 2

Filter with MW cutoff size 50K was evaluated to limit the escape of mAb from the filter. In addition, the effects of the centrifugation speed (13,000, 7,000 rpm) to the filtration separation was also evaluated. The results of the effects of these two factors with four conditions in total are shown in Table 2. When the speed was 13,000 rpm, 8 minutes were applied while for 7000 rpm, 15 minutes were used so the final solution of the samples reached to the same volume. The total amount of the sample was decreased substantially from 1.5 mg to less than 16 μg after the filtration for all four conditions, indicating about 100 times sample removal by filtration. For the antibody mAb1 used, compared to the 100K filter, 50K filter blocked significantly more amount of antibody with final peptide amount less than 1 μg. 50K filter with 13,000 rpm for 8 minutes was the best condition which resulted in highest total protein identification with high confidence (Table 2).

TABLE 2

| Denature Buffer | Filter | Speed (rpm) | Time (min) | Final peptide amount | Total ID | Match to IP's result (confirmed) | High confidence protein No. (>2 peptide) |
|---|---|---|---|---|---|---|---|
| 1 SDC + SLS | 100K | 13,000 | 8 | 8.6 μg | 135 | 7 | 34 |
| 2 SDC + SLS | 100K | 7000 | 15 | 16 μg | 129 | 5 | 23 |
| 3 SDC + SLS | 50K | 13,000 | 8 | 0.68 μg | 173 | 10 | 61 |
| 4 SDC + SLS | 50K | 7000 | 15 | 0.56 μg | 156 | 10 | 52 |

Figure 2:
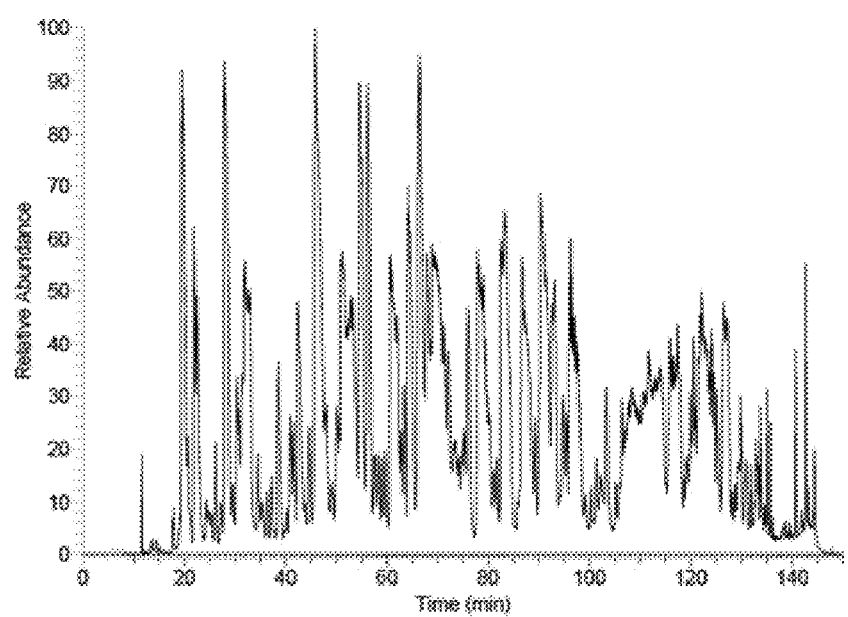
FIG. 2 shows the total ion chromatography graph obtained from direct digestion of NIST standard.
Figure 3:
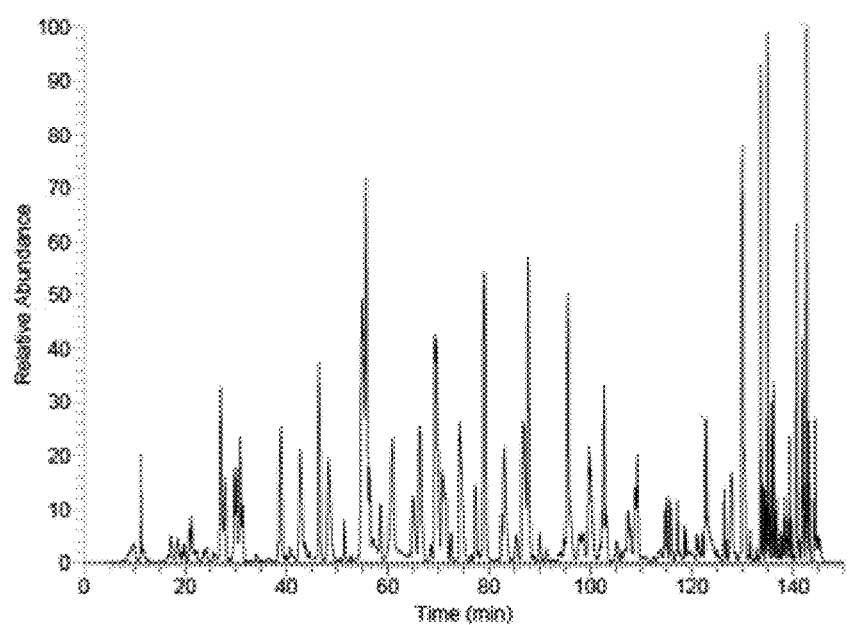
FIG. 3 shows the total ion chromatography graph obtained from NIST standard treated with HCP identification method according to an exemplary embodiment.
Figure 4:
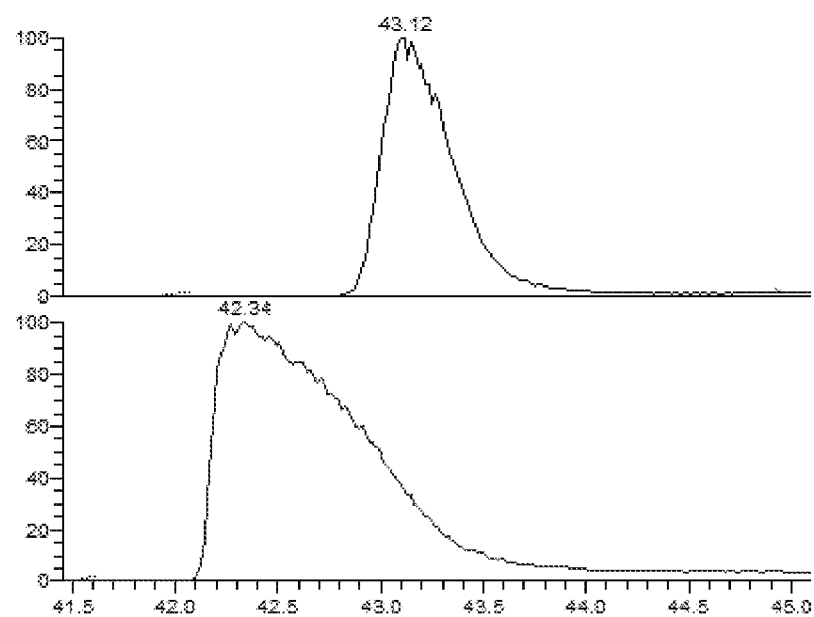
FIG. 4 shows the XIC of one peptide with m/z $546.60^{3+}$ without and with the HCP identification method according to an exemplary embodiment.

For the filtration performed using 50K filter with 13,000 rpm for 8 minutes, FIGS. 2 and 3 showed the total ion chromatography of the sample before and after filtration, respectively. With same amount of sample injection after filtration, the mass spectra of filtered sample were much cleaner than the one before filtration (FIGS. 2 and 3), suggesting drastic sample reduction. The sample reduction can also be seen from XIC profile of individual antibody peak. For example, compared to the sample treated by filtration, the XIC of the peak with m/z of $546.60^{3+}$ without filtration showed a significant reduction in the apex retention with a typical right sided "shark pin" shape, indicating a significant overloading of the sample (FIG. 4). It should be noted that the overall injection amount is approximately the same, therefore, it was the antibody in the sample drastically reduced by filtration method, resulting in a sample with relatively less antibody but more HCPs. Therefore, the identification of HCPs was improved significantly.

Example 3

Figure 5:
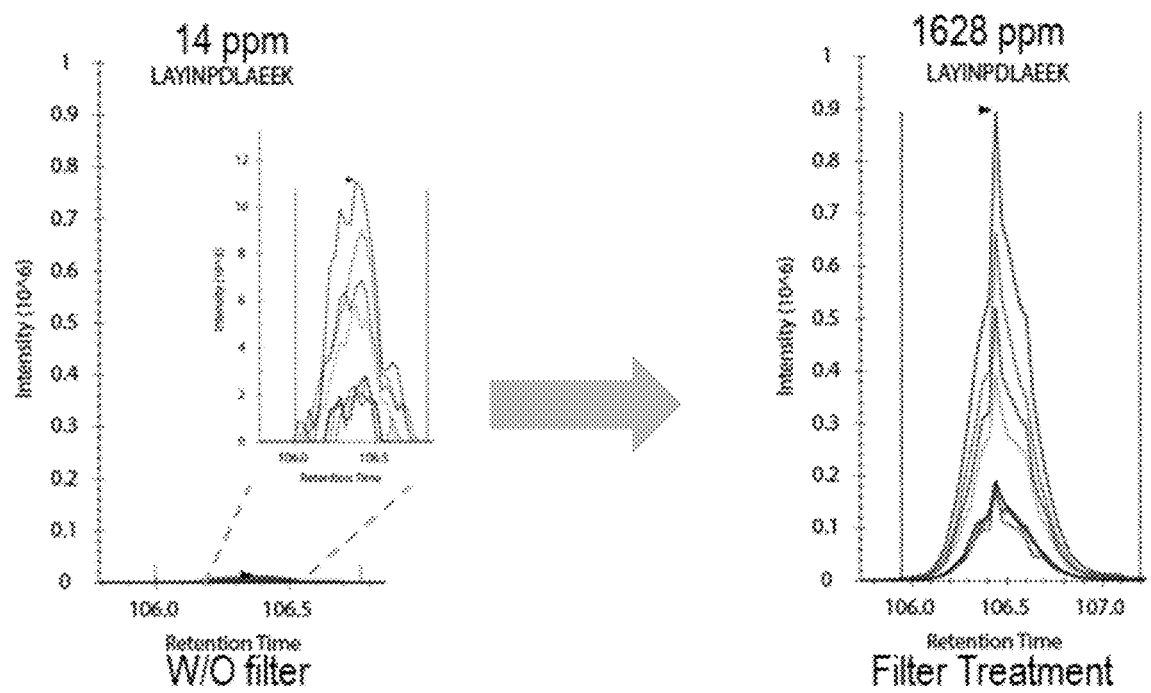
FIG. 5 shows a targeted quantitation (PRM) of peptide LAYINPADLAEEK from stress-induced phosphoprotein 1 in NIST standard before and after the HCP identification method according to an exemplary embodiment.

To evaluate the exact amount of the sample reduction or the inversed HCP enrichment occurring in filtration process, a parallel reaction monitoring (PRM) was performed with a targeting MS approach to calculate the HCP enrichment factor by filter method. By comparing relative abundance of individual HCP peptides versus antibody peptides (for mAb1) before and after filtration, the HCP enrichment factor can be calculated. FIG. 5 shows that the PRM signal changes of one HCP peptide, LAYINPDLAEEK. More than 100-fold increase of signal was observed, with relative abundance increased from 14 ppm to 1628 ppm by filtering out the antibody (FIG. 5). By eliminating most of antibody with the filter, the concentration range of the filtered solution is greatly reduced so that the relative concentration of HCPs is much higher thus visible in subsequent MS analysis.

Example 4

To evaluate the detection limit of the HCP identification method, a spiked-in experiment was conducted. Twelve (12) proteins including 11 CHO proteins and 1 human protein with varying concentrations ranging from 0.1 to 200 ppm were spiked into one purified monoclonal antibody (mAb1) with very low level of HCPs. Since the evaluation of the size effect of MW cutoff filter was being carried out, the 12 selected proteins not only varied in concentration, but also in molecular weight/size, ranging from 14.6 KDa to 86.5 KDa (Table 3). The results showed that size did matter when M.W cutoff filtration was applied. PLBD2 and human PCSK9 are proteins with size of 65.5 and 74.3 KDa, respectively, well above 50 KDa cutoff After 50 KDa cutoff filtration, both proteins were not detected. However, if the amount of a larger molecule e.g., Glutathione-S-transferase Mu6 (86.5 KDa) was very high, the protein could pass through the filter in spite of higher than M.W cutoff molecular weight. This can also explain why antibody can always survive the filter blockade. For low level of spiked-in proteins, 0.5 ppm of acid ceramidase with 4 unique peptides whereas only 1 unique peptide was detected for 1 ppm Transthyretin. Typically in shotgun proteomic analysis, the smaller size of protein gets the less chance to be detected due to the fact that proteins with small size generate much less peptides than larger proteins. Another reason for this high confidence identification could contribute to the high ionization efficiency of some specific tryptic peptides from acid ceramidase. Nevertheless, the HCP identification method demonstrates that the detection limit of filtration method is in the range of 0.5 to 1 ppm.

TABLE 3

| Spiked in ppm | Protein Name | Uniprot Accession | # Peptides | # PSMs | # Unique Peptides | MW [KDa] |
|---|---|---|---|---|---|---|
| 200 | Glutathione-S-transferase Mu6 | G3IKC3 | 7 | 19 | 7 | 86.5 |
| 100 | Annexin A1 | G3I5L3 | 10 | 41 | 10 | 38.8 |
| 50 | Heavy PLBD2 | G3I6T1 | 0 | 0 | 0 | 65.5 |
| 20 | Cathepsin Z | G3I4W7 | 14 | 200 | 14 | 44.1 |
| 10 | TIMP1 | G3IBH0 | 2 | 12 | 2 | 22.4 |
| 10 | Antileukoproteinase | G3HLT0 | 7 | 89 | 7 | 14.6 |
| 5 | C-X-C motif chemokine | A4URF0 | 4 | 47 | 4 | 39.7 |
| 5 | Hamster lysosomal acid lipase | G3HQY6 | 1 | 2 | 1 | 45.6 |
| 1 | PLBD2 | G3I6T1 | 0 | 0 | 0 | 65.5 |
| 1 | Transthyretin | G3I4M9 | 1 | 3 | 1 | 15.8 |
| 0.5 | Acid Ceramidase | G3GZB2 | 4 | 12 | 4 | 44.7 |
| 0.1 | human PCSK9 | Q8NBP7 | 0 | 0 | 0 | 74.3 |

Example 4

Figure 6:
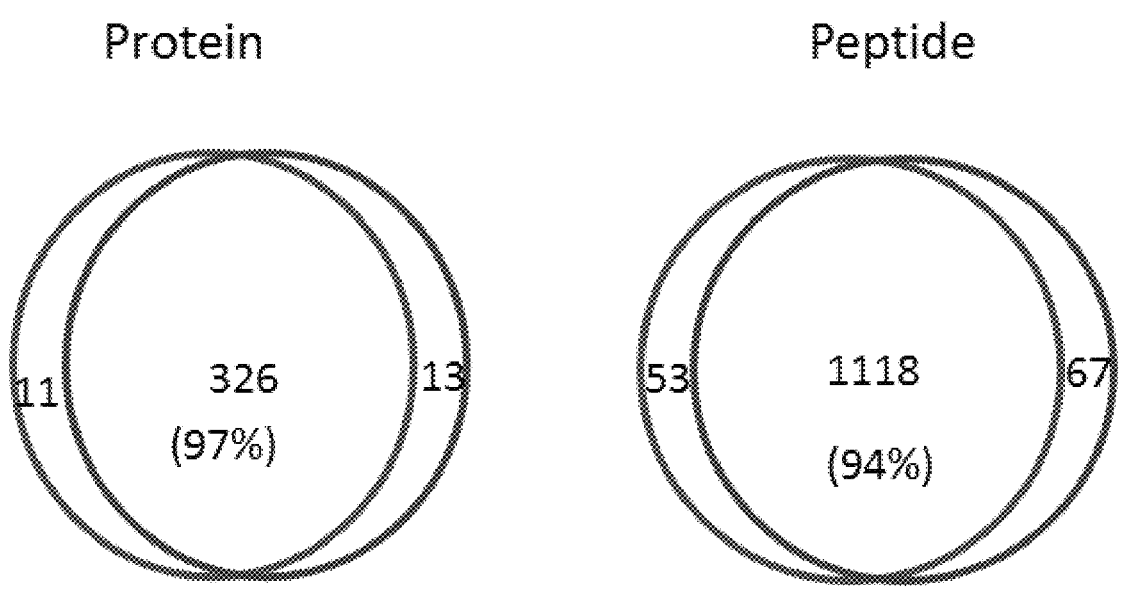
FIG. 6 shows a Venn diagram that identifies proteins and peptides overlapped between duplicated runs of HCP identification method performed according to an exemplary embodiment.
Figure 7:
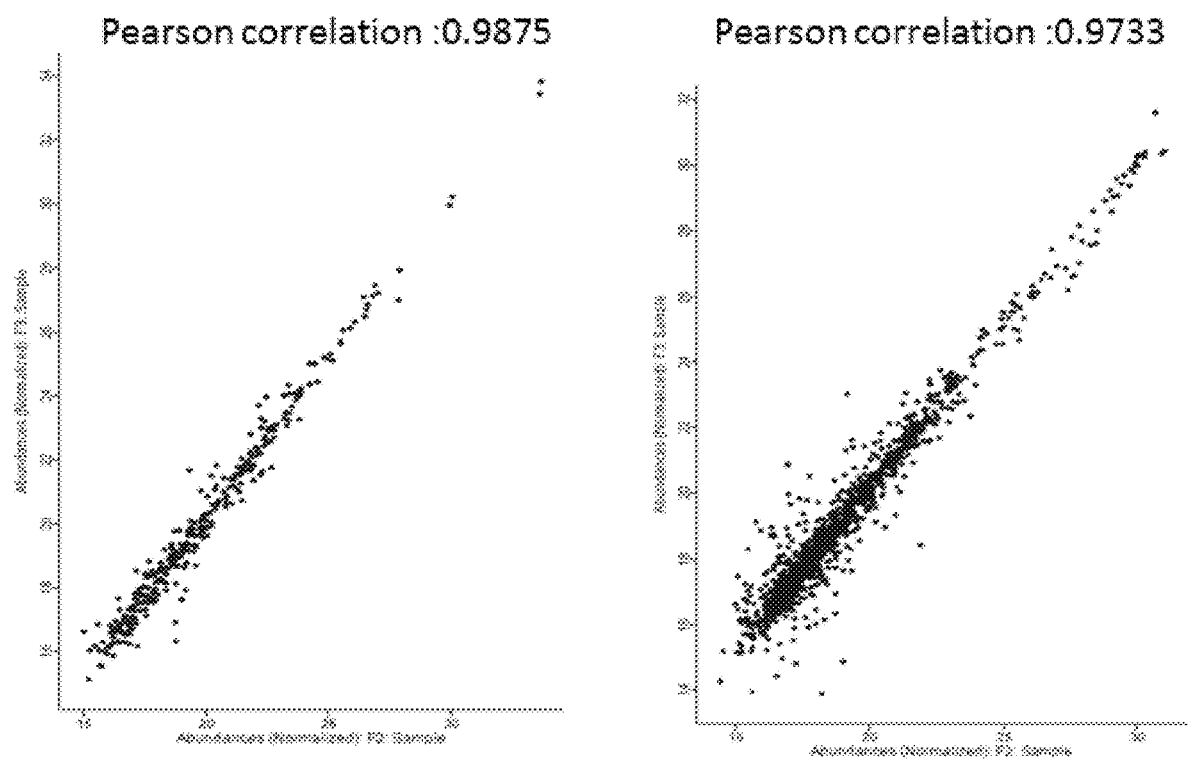
FIG. 7 shows a comparison of protein and peptide intensities in two individual duplicated runs of HCP identification method performed according to an exemplary embodiment.

A duplicate experiment using NIST standard was carried out to evaluate the reproducibility of this method. In total, 326 proteins equivalent to 97% of proteins and 1118 peptides equivalent to 94% peptides were identified in both runs, respectively (FIG. 6). The highly repeatable results also indicate the high confidence in protein identification which is crucial in HCP study. Label-free quantitation was performed to quantify the relative amount of each peptides in both runs, more than 0.97 Pearson correlation representing this method is highly reproducible with little variation (FIG. 7).

Example 5

Figure 8:
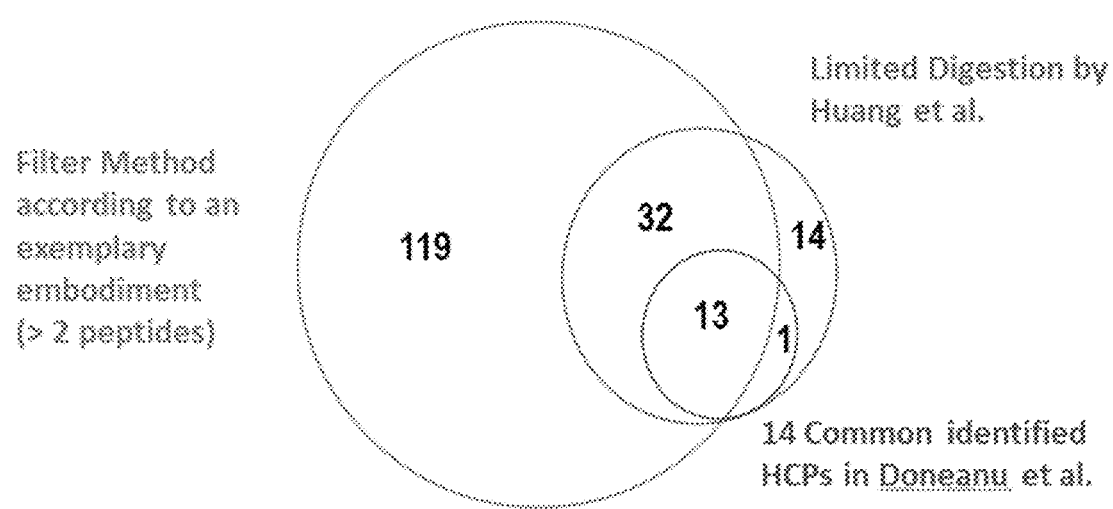
FIG. 8 shows a Venn diagram of the identification comparison between the HCP identification method performed according to an exemplary embodiment, limited digestion and 2D LC-MS/MS methods.

Many powerful mass spectrometry based approaches have been published to characterize HCPs in specific biopharmaceutical products that are not available for other researchers, thus it is almost not possible to directly compare results across different methods. Recently, both Doneanu et al. (supra) and Huang et al. (supra) applied their method on NIST antibody standard RM 8670 and identified 14 and 59 high confidence HCPs, respectively. To facilitate a direct comparison, the HCP identification method to characterize the HCPs in NIST RM 8670 standard was performed. 164 mouse proteins were identified with high confidence (more than 2 peptides) and false positive rate ≤0.01. As shown in FIG. 8, 13 of 14 and 45 of 59 HCPs that were detected by Doneanu et al. (supra) and Huang et al. (supra), respectively, were identified. The unidentified proteins by these methods are either those with molecular weight higher than 50 KDa or are ambiguous low abundance targets (Table 4). In summary, 119 mouse HCPs in NIST antibody standard identified by the HCP identification method were not reported in previous two studies. Among them, 38 of 119 proteins contains more than 5 unique peptides, and 90 for ≥3 peptides.

TABLE 4

| accession | description | size | unique pep | inj. no. 1 | inj. no. 2 | inj. no. 3 | average |
|---|---|---|---|---|---|---|---|
| Q8C7U7 | polypeptide N-acetylgalactosaminyltransferase 6 | 71.9 | 10 | 5 | 7 | 6 | 6 |
| Q62179 | semaphorin-4B | 91.4 | 7 | 5 | 10 | 5 | 6 |
| Q6PB93 | polypeptide N-acetylgalactosaminyltransferase 2 | 64.5 | 7 | 3 | 3 | 3 | 3 |
| P40124 | adenylyl cyclase-associated protein 1 | 51.6 | 4 | 0.8 | 0.8 | 0.8 | 0.8 |
| P11680 | properdin | 50.3 | 3 | 1 | 2 | 1 | 2 |
| Q8BND5 | sulfhydryl oxidase 1 | 82.8 | 3 | 2 | 2 | 2 | 2 |
| Q9QUR8 | semaphorin-7A | 75 | 2 | 1 | 1 | 1 | 1 |
| P09041 | phosphoglycerate kinase 2 | 44.9 | 2 | 1 | 1 | 1 | 1 |
| P03975 | IgE-binding protein | 62.8 | 2 | 1 | 1 | 1 | 1 |
| Q9CQF3 | cleavage and polyadenylation specificity factor subunit 5 | 26.2 | 2 | 1 | 1 | 1 | 1 |
| P34902 | cytokine receptor common subunit gamma | 42.2 | 2 | 1 | 1 | <0.5 | 1 |
| Q6PDM2 | serine/arginine-rich splicing factor 1 | 27.7 | 2 | <0.5 | <0.5 | 1 | <0.5 |
| Q6PGH2 | hematological and neurological expressed 1-like protein | 20 | 2 | <0.5 | <0.5 | <0.5 | <0.5 |
| P19157 | glutathione S-transferase P | 23.6 | 2 | <0.5 | <0.5 | <0.5 | <0.5 |

Example 6

The validation of known and novel HCPs in NIST was carried out by parallel reaction monitoring.

To verify the targets that found by the HCP identification method, 27 identified NIST HCPs were randomly selected to subject to PRM analysis. By comparing peptide signals of these HCPs before and after filtration treatment, a validation of these proteins was provided with an improved efficiency of this method. All the selected targets were found to be enriched 2 to 120 times by the HCP identification method (Table 5 and 6). Table 5 lists the targets that have been identified by other two studies. 70% of selected targets were measured to be higher than 1 ppm in direct digest sample, consistent with the results from Huang et al. (supra) in which more than 80% of the targets were found to be more than 1 ppm. Table 6 lists the novel targets that were detected by the HCP identification method only. The results clearly showed drastically improved efficacy. Most of the proteins measured were below 0.5 ppm before filtration treatment. However after filtration, the relative concentrations of the proteins increased such that they could be easily detected. The improved efficacy for these low abundancy proteins are prominent, most with over 100 times and some with 1000 times improvement. The fact that much more identified low abundance targets suggests the importance of the key factor in this method: reduction of dynamic range. The dynamic range composed by antibody and its associated HCPs was reduced 3 orders of magnitude, approximately from 8 orders to 5 orders, hence magnify the HCPs signal.

The above examples present a simple and powerful method to identify HCPs in a sample matrix having a protein of interest by applying one single step of molecular weight cut-off filtration followed by basic proteomic approaches, such as, shotgun proteomics. This procedure can successfully be used to remove majority of the protein of interest in a sample matrix, therefore dramatically reduced the dynamic range in the sample matrix leading to a much more improved detection of low abundant HCPs.

TABLE 5

| Accession No. | Protein Name | Direct digest (ppm) | Filter treatment (ppm) |
|---|---|---|---|
| P08101 | low affinity immunoglobulin gamma Fc region receptor II | 56.5 | 456 |
| P01887 | Beta-2-microglobulin | 44.97 | 4214.69 |
| P05063 | Fructose-bisphosphate aldolase C | 82.87 | 1265.41 |
| P05064 | Fructose-bisphosphate aldolase A | 366.63 | 2023.93 |
| P10126 | Elongation factor 1-alpha 1 | 4.8 | 51.4 |
| P32020 | Non-specific lipid-transfer protein | 0.98 | 137.10 |
| P35700 | Peroxiredoxin-1 | 0.64 | 27.6 |
| P53996 | Cellular nucleic acid-binding protein | 0.58 | 60.04 |
| P99029 | Peroxiredoxin-5, mitochondrial | 2.59 | 122.41 |
| Q60864 | Stress-induced-phosphoprotein 1 | 14.64 | 1627.93 |
| Q8BL97 | Serine/arginine-rich splicing factor 7 | 8.05 | 783.78 |
| Q8CGC7 | Bifunctional glutamate/proline--tRNA ligase | 0.53 | 13.17 |
| Q91YR9 | Prostaglandin reductase 1 | 4.65 | 53.05 |
| Q922R8 | Protein disulfide-isomerase A6 | 12.69 | 25.53 |
| Q923D2 | Flavin reductase | 3.37 | 145.17 |
| Q9D8B3 | Charged multivesicular body protein 4b | 0.12 | 31.62 |
| Q9Z0X1 | Apoptosis-inducing factor 1, mitochondrial | 2.34 | 63.62 |

TABLE 6

| Accession No. | Protein Name | Direct digest (ppm) | Filter treatment (ppm) | Improved efficacy |
|---|---|---|---|---|
| O08583 | THO complex subunit 4 | 8.02 | 1716.65 | 214 |
| P14152 | Malate dehydrogenase, cytoplasmic | 0.28 | 124.66 | 445 |
| P16858 | Glyceraldehyde-3-phosphate dehydrogenase | 0.32 | 52.3 | 163 |
| P52480 | Pyruvate kinase PKM | 0.02 | 9.35 | 468 |
| P60335 | Poly(rC)-binding protein 1 | 5.33 | 161.00 | 30 |
| Q05816 | Fatty acid-binding protein 5 | 0.10 | 10.94 | 109 |
| Q80U87 | Ubiquitin carboxyl-terminal hydrolase 8 | 0.01 | 13.34 | 1334 |
| Q9DB15 | 39S ribosomal protein L12, mitochondrial | 0.34 | 74.10 | 218 |

TABLE 6-continued

| Accession No. | Protein Name | Direct digest (ppm) | Filter treatment (ppm) | Improved efficacy |
|---|---|---|---|---|
| Q9CR16 | Peptidyl-prolyl cis-trans isomerase D | 0.37 | 105 | 284 |
| Q9CZY3 | Ubiquitin-conjugating enzyme E2 variant 1 | 8.4 | 66.7 | 8 |

What is claimed is:

1. A method for identifying a host-cell protein in a sample matrix having a protein of interest, comprising the steps of:
   a) dissociating the host-cell protein from the protein of interest, wherein the host cell protein is not the protein of interest;
   b) filtering and centrifuging the dissociated host-cell protein using a molecular weight cut-off filter with a cutoff of at least 30 kDa, thus obtaining a filtered host-cell protein that has a molecular weight lower than the molecular weight of the molecular weight cutoff filter;
   c) subsequently mixing the filtered host cell protein with a hydrolyzing agent in order to digest the filtered host-cell protein; and identifying the filtered host-cell protein.

2. The method of claim 1, wherein the protein dissociation is carried out using a protein dissociating agent.

3. The method of claim 1 further comprising contacting the filtered host-cell protein with a protein reducing agent.

4. The method of claim 1 further comprising contacting the filtered host-cell protein to a protein alkylating agent.

5. The method of claim 1 further comprising centrifuging the host-cell protein at about 13,000 rpm for about 8 minutes.

6. The method of claim 1, wherein the protein of interest is an antibody.

7. The method of claim 1, wherein the protein of interest is a therapeutic antibody.

8. The method of claim 1, wherein the identification of the host-cell protein of step (c) is carried out using a mass spectrometer.

9. The method of claim 8, wherein the mass spectrometer is coupled to a liquid chromatography system.

10. The method of claim 9, wherein the liquid chromatography system is a nano liquid chromatography system.

11. The method of claim 8, wherein the mass spectrometer is a tandem mass spectrometer.

12. The method of claim 1, wherein the molecular weight cut-off filter has a cutoff of about 100 KDa.

13. The method of claim 1, wherein the molecular weight cut-off filter has a cutoff of about 50 KDa.

14. The method of claim 1, wherein the protein dissociating agent is degradable.

15. The method of claim 1, wherein a detection limit of the host-cell protein is at least about 1 ppm.

16. The method of claim 1, wherein the filtering step enriches the dissociated host-cell protein by at least about 50-fold as compared to the sample matrix.

17. The method of claim 1, wherein a detection limit of a host-cell protein is at least about 5-fold greater than a detection limit of another method not comprising a step for filtering the dissociated host-cell protein using a molecular weight cut-off filter.

18. A method for identifying a host-cell protein in a sample matrix having a protein of interest, comprising:
   a) dissociating the host-cell protein from the protein of interest using a protein dissociating agent, wherein the host cell protein is not the protein of interest;
   b) filtering the dissociated host-cell protein using a molecular weight cut-off filter of at least 30 kDa, to thus obtaining a filtered host-cell protein solution that has a molecular weight lower than the molecular weight of the molecular weight cutoff filter, wherein the filtering enriches the dissociated host-cell protein in the filtrate by at least about 50-fold as compared to the sample matrix; and
   c) identifying the host-cell protein in the filtered host cell-protein solution using a mass spectrometer.

19. A method for identifying a host-cell protein in a sample matrix having a protein of interest, comprising:
   a) dissociating the host-cell protein from the protein of interest using a protein dissociating agent, wherein the host cell protein is not the protein of interest;
   b) filtering the dissociated host-cell protein using a molecular weight cut-off filter, of at least 30 kDa, thus obtaining a filtered host-cell protein that has a molecular weight lower than the molecular weight of the molecular weight cutoff filter;
   c) wherein the filtering enriches the dissociated host-cell protein in the filtrate by at least about 50-fold as compared to the sample matrix;
   d) subsequently mixing the filtered host cell protein with a hydrolyzing agent in order to digest the filtered host-cell protein; and
   e) identifying the host-cell protein using a mass spectrometer.

* * * * *